United States Patent [19]

Ben-Hur et al.

[11] Patent Number: 5,895,786
[45] Date of Patent: Apr. 20, 1999

[54] METHOD FOR TREATING VIRAL INFECTIONS

[75] Inventors: Ehud Ben-Hur, New York, N.Y.; Zvi Malik, Emek Hefer, Israel

[73] Assignee: New York Blood Center, Inc., New York, N.Y.

[21] Appl. No.: 08/646,548

[22] Filed: May 8, 1996

[51] Int. Cl.$^6$ .................. A61K 31/195; A61K 31/40
[52] U.S. Cl. .................. 514/561; 514/410; 514/185
[58] Field of Search .................. 514/410, 561, 514/185; 540/145; 562/567

[56] References Cited

U.S. PATENT DOCUMENTS 5,484,803  1/1996  Richter .................. 514/410

OTHER PUBLICATIONS

Lofgren LA et al. Br. J. Cancer, 72, 857–864, 1995.
Iinuma S et al. Br. J. Cancer, 70, 21–28, 1994.

*Primary Examiner*—Evelyn Huang
*Attorney, Agent, or Firm*—Amster, Rothstein & Ebenstein

[57] ABSTRACT

The present invention provides a method for treating a viral infection in a subject. The method comprises administering to the subject an amount of 5-aminolevulinic acid and an iron-chelating agent to cause virus-infected cells to accumulate protoporphyrin in amounts such that upon application of a sufficient dose of red light, the virus-infected, protoporphyrin-accumulated cells will be destroyed; and applying a sufficient dose of red light to the virus-infected, protoporphyrin-accumulated cells to destroy the virus-infected, protoporphyrin-accumulated cells.

6 Claims, 7 Drawing Sheets

METHOD FOR TREATING VIRAL INFECTIONS

BACKGROUND OF THE INVENTION 5-aminolevulinic acid (ALA) is a precursor of haem biosynthesis and its synthesis is a rate-limiting step in this pathway. When ALA is supplied to certain cells exogenously, protoporphyrin IX is accumulated in the cells because conversion of protoporphyrin to haem by ferrochelatase becomes rate-limiting (Malik, Z. and M. Djaldetti, *Cell Different.* 8:223-233 (1979)). Because protoporphyrin is a photosensitizer, subsequent exposure to light leads to cell destruction, primarily by damage to the mitochondria (Linuma, S., et al., *Br. J. Cancer* 70:21-28 (1994)).

Photodynamic therapy mediated by ALA was proposed in 1990 as a new cancer treatment (Kennedy, J. C., et al., *J. Photochem. Photobiol. B:Biol.* 6:143-148 (1990)). Topical application of ALA followed by exposure to light has been used successfully for eradication of various skin cancers in clinical studies (Kennedy, J. C. and R. H. Pottier, *J. Photochem. Photobiol. B:Biol.* 14:275-292 (1992); Fijan, S., et al., *Br. J. Dermatol.* 133:282-288 (1995); Roberts, D. J. H. and F. Cairnduff, *Br. J. Plastic Surg.* 48:360-370 (1995)). In addition, the combination of ALA and light has been suggested for treating mycosis fungoides (Wolf, P., et al., *J. Am. Acad. Dermatol.* 31:678-680 (1994)), as well as the ablation of the endometrium as an alternative to hysterectomy or for sterilization (Yang, J. Z., et al. *Am. J. Obst. Gynecol.* 68:995-1001 (1993)). However, prior to the present invention, the combined use of ALA and light has not been demonstrated to be useful for inactivating intracellular viruses either in vitro or in vivo.

SUMMARY OF THE INVENTION

The present invention provides a method for treating a viral infection in a subject comprising administering to the subject an amount of 5-aminolevulinic acid to cause virus-infected cells to accumulate protoporphyrin in amounts such that upon application of a sufficient dose of red light, the virus-infected, protoporphyrin-accumulated cells will be destroyed; and applying a sufficient dose of red light to the virus-infected, protoporphyrin-accumulated cells to destroy the virus-infected, protoporphyrin-accumulated cells.

The present invention also provides a method for destroying virus-infected cells contained in blood or a cellular component thereof in vitro comprising treating the blood or cellular component thereof with an amount of 5-aminolevulinic acid to cause virus-infected cells contained in the blood or cellular component thereof to accumulate protoporphyrin in amounts such that upon application of a sufficient dose of red light, the virus-infected, protoporphyrin-accumulated cells will be destroyed; and applying a sufficient dose of red light to the virus-infected, protoporphyrin-accumulated cells to destroy the virus-infected, protoporphyrin-accumulated cells contained in the blood or cellular component thereof.

Additional objects of the present invention will be apparent from the description which follows.

DETAILED DESCRIPTION OF THE INVENTION

Figure 1:
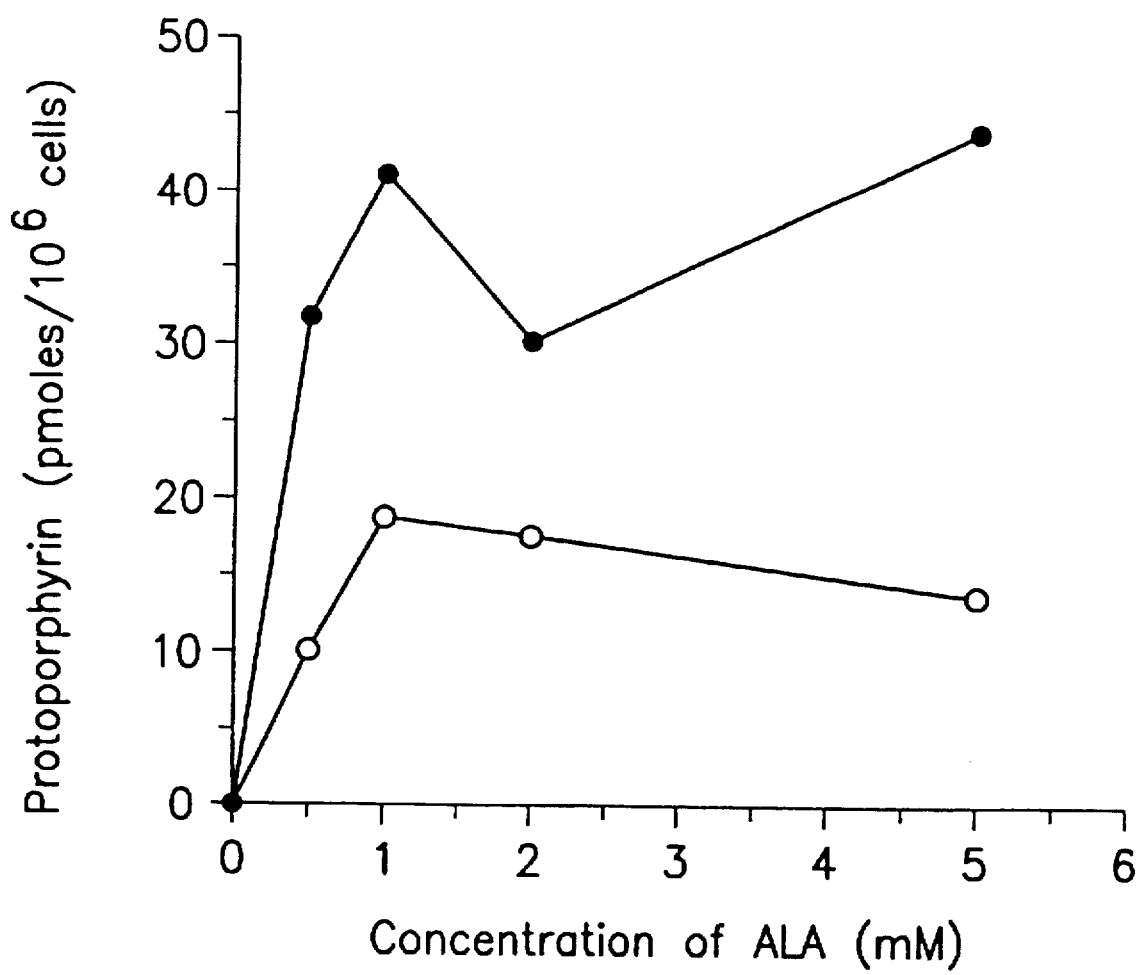
FIG. 1 represents the accumulation of protoporphyrin in U1 cells upon incubation for 5 hours in growth medium with various mM concentrations of ALA alone (○) and in combination with 50 μM desferal (●). The cells were then extracted with 1M HCL and protoporphyrin content was measured using spectrofluorimetery.

The present invention provides a method for treating a viral infection in a subject in need of such treatment. In the method of the present invention, an amount of ALA is administered to the subject to cause virus-infected cells to accumulate protoporphyrin in amounts such that upon application of a sufficient dose of red light, the virus-infected, protoporphyrin-accumulated cells will be destroyed. After protoporphyrin is accumulated in the virus-infected cells, red light is applied to the virus-infected, protoporphyrin-accumulated cells at a sufficient dose to destroy the virus-infected, protoporphyrin-accumulated cells, thereby treating the viral infection.

As used herein, "virus-infected cells" refers to cells infected with a virus, and includes but is not limited to red blood cells, platelets, lymphocytes, monocytes, macrophages, endothelial cells, epithelial cells and neuronal cells. Preferably, the infected cells are epithelial cells. "Destroy" means that the virus infected cells are destroyed or impaired in such a manner so as to destroy, inactivate or render non-functional the virus contained in the cells. The "subject" may be a human or an animal subject, and is preferably a human subject.

The method of the present invention may be used to treat various viral infections caused by intracellular viruses, and particularly viruses which result in cells infected therewith to have elevated levels of protoporphyrin upon addition of ALA to the infected cells. Preferred viruses include but are not limited to herpes simplex virus, Molluscum contagiosum virus, human immunodeficiency virus, Varicella zoster virus, C-type retrovirus, Ebstein-Barr virus, cytomegalovirus and papillomavirus. Particularly preferred viruses include viruses which infect epithelial cells such as herpes simplex virus, Molluscum contagiosum virus and papillomavirus, resulting in conditions such as lesions, warts, papillomas, Verrucae vulgares and the like.

ALA may be administered by conventional modes of administration such as oral, topical, or parenteral administration. The mode of administration will generally depend upon whether the viral infection is systemic or localized. If the viral infection is localized to the epithelial cell layer, for example, (e.g. herpes simplex virus, Molluscum contagiosum or papillomavirus), it is preferred, that ALA be administered topically. On the other hand, if the viral infection is systemic (e.g. human immunodeficiency virus, Varicella zoster virus, C-type retrovirus or Ebstein-Barr virus), it is preferred that ALA be administered parenterally.

For oral, topical, or parenteral administration, ALA may be combined with a pharmaceutically acceptable carrier which is "acceptable" in the sense of being, compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The formulations may conveniently be presented in unit dosage and may be prepared by methods well-known in the pharmaceutical art, by bringing ALA into association with a carrier or diluent, as a suspension or solution, and optionally one or more accessory ingredients, e.g. buffers, flavoring agents, surface active agents, and the like. The choice of carrier will depend upon the route of administration.

For oral administration, ALA may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

For parenteral administration (i.e. intravenous, subcutaneous, intramuscular or intraperitoneal administration), ALA may combined with a sterile aqueous solution which is preferably isotonic with the blood of the recipient. Such formulations may be prepared by dissolving ALA in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For topical administration, ALA may be combined with creams, gels, oils and the like. Skin penetration enhancers such as dimethylsulfoxide (DMSO), propylene glycol, polyethylene glycol, isopropanol, ethanol, oleic acid, N-methylpyrrolidone, and the like, which increase the permeability of the skin to ALA, also may be employed. In addition, ALA may be combined with a polymeric substance such as ethylcellulose, hydroxypropyl cellulose, ethylene/vinylacetate, polyvinyl pyrrolidone, and the like, to provide the composition in gel form, which can be dissolved in solvent such as methylene chloride, evaporated to the desired viscosity, and then applied to backing material to provide a patch.

The amount of ALA administered is an amount effective to cause the virus-infected cells to accumulate protoporphyrin in amounts such that upon application of a sufficient dose of red light, the protoporphyrin is activated and undergoes a reaction which destroys the virus-infected cells. The amount of ALA administered will depend upon the route of administration as well as the type and extent of viral infection, and is readily determinable by one skilled in the art. Generally, the amount of protoporphyrin accumulated in the cells should be between about 20 pmoles and about 100 pmoles per $10^6$ cells. This amount will be accumulated within about 3 to about 6 hours following administration of ALA.

It is also within the confines of the present invention that the accumulation of protoporphyrin may be enhanced by administrating an iron chelating agent along with ALA. The iron chelating agent enhances the accumulation of protoporphyrin because it inhibits the conversion of protoporphyrin to haem by ferrochelatase in the virus-infected cells. Suitable iron chelating agents include EDTA and desferal. However, other iron chelating agents may be employed.

After protoporphyrin is accumulated in the virus-infected cells, red light is applied to the virus-infected cells at a sufficient dose to destroy the viral-infected cells. As used herein, "red light" corresponds to a wavelength of light which causes ALA to undergo a photochemical reaction, and may be a narrow band corresponding to the maximum absorption of protoporphyrin, i.e. 630 nm, or a broad band (e.g. 590-700 nm) which encompasses the absorption of protoporphyrin. The dose of light is a function of the intensity and duration of light applied. The dose applied will depend upon whether the viral infection is systemic or localized, as well as the extent of the viral infection. Suitable sources of light include commercially available lasers, lamps, light emitting diodes and the like. Preferably, a 500 W xenon short arc lamp (Versa Light, Medic Lightech, Ltd., Haifa, Israel) is employed. To achieve the desired wavelength of light, the lamp may be equipped with commercially available filters.

The present invention also provides a method for destroying virus-infected cells contained in blood or a cellular component thereof in vitro. In this method, the blood or cellular component thereof is treated with an amount of ALA to cause virus-infected cells contained in the blood or cellular component thereof to accumulate protoporphyrin in amounts such that upon application of a sufficient dose of red light, the virus-infected, protoporphyrin-accumulated cells will be destroyed. After the protoporphyrin is accumulated in the virus-infected cells, a sufficient dose of red light is applied to the virus-infected cells to destroy the virus-infected cells.

This method may be used to destroy virus-infected cells that may be present in blood or cellular components of blood collected by blood banks, hospitals and the like. This method also may be used to treat viral infections by removing blood from the subject, treating the blood or a cellular component thereof which contains the virus-infected cells with the combination of ALA and red light, and reintroducing the blood and/or cellular component thereof back into the patient. As used herein, "cellular component" refers to the cells contained in blood which contain viruses, and includes but is not limited to red blood cells, platelets, lymphocytes, monocytes and macrophages.

The present invention is described in the following Experimental Details Section which is set forth to aid in an understanding of the invention, and should not be construed to limit in any way the invention as defined in the claims which follow thereafter.

EXPERIMENTAL DETAILS SECTION

Materials and Methods

Cell lines. Raji cell line was persistently infected with *Varicella zoster* virus (VZV) as well as a retrovirus (c-type). P3HR1 cell line was persistently infected with Epstein-Barr virus (EBV). Both cell lines were cultured in RPMI 1640 growth medium supplemented with 2 mM glutamine, 250 U/ml of penicillin, 250 µg/ml of streptomycin and 10% fetal calf serum (FCS).

CEM-SS cell line (obtained from Dr. Peter L. Nara, NCI Frederick Cancer Research and Development Center, USA) was persistently infected with herpes simplex virus type-1 (HSV-1). The uninfected cells were maintained as a stationary suspension cultured at 37° C. At 3 to 4 days after subculture, the CEM cells were washed twice with 10 ml of RPMI 1640 medium without serum and centrifuged at 300×g for 10 minutes. The cell pellet was infected with HSV-1 (multiplicity of infection 1.0). The cells were incubated with shaking for 1 hour at 37° C. After viral adsorption the cells were washed twice with RPMI to remove excess unabsorbed virus. Infected and uninfected cells were resuspended to a final concentration of $5 \times 10^5$ cells per ml in RPMI 1640 with 10% FCS. At 4–5 day intervals, the cells were assayed for the presence of HSV by an immunological method.

U1 cells latently infected with HIV (Folks, T.M., et al., *Science* 238:800–802 (1987)) were obtained from Dr. Thomas Folks, National Institutes of Health and cultured as above. Following treatment, the cells were induced to express HIV by addition of 100 ng/ml of phorbol 12-myristate 13-acetate (PMA; Sigma Chemical Co.) for 24 hr. The cultures were then rinsed twice and production of HIV was measured by focal immunoassay (Chesboro, B. and K. Wehrly, *J. Virol.* 62:3779–3788 (1988)).

Primary cell culture. Peripheral blood mononuclear cells (PBMC) were prepared from healthy donors. Venous blood mixed with heparin (25 µg/ml) was separated on a Ficol-Hypaque (1.4 g/ml). Rich white blood cell band was rinsed in RPMI 1640 and resuspended at $1 \times 10^6$ cells per ml RPMI 1640+20% FCS. The cells were stimulated to proliferate by 5 µg/ml phytohemagglutinin (PHA) at 37° C. at 5% $CO_2$. The cells were used for photodynamic treatment (PDT) experiments after 3 days in culture.

Immunofluorescence assay (IF). The HSV, VZV and EBV antigens were detected by methods previously described. Non-fixed cells were used for the indirect IF for HSV and VZV. Acetone fixed cells were used for the EBV indirect IF. The antigens were detected by employing serum containing antibodies to HSV (titer 1:512) that is free of antibodies to EBV or VZV; serum containing antibodies to VZV (titer 1:512) that is free of antibodies to HSV or EBV, and serum containing no antibodies to HSV, VZV and EBV. Percentage of cells showing fluorescence was calculated.

XTT assay. Cellular growth or survival after PDT was determined. 2–3 bis|2-methoxy-4-nitrosulfophenyl|-5-|(phenyl-amino)carbomyl|-2-H-tetrasodium hydroxide (XTT) (Sigma Chemical Co.) was prepared at 1 mg/ml in prewarmed (37° C.) medium without serum. Phenazine methosulfate (PMS, Sigma) at 5 nM in PBS was prepared and stored as a stock solution at −20° C. 50 µl of a mixture containing 50 µg XTT and 0.38 µg PMS was added to each well in 96 microtiter plates. After a 4 hour incubation at 37° C., absorbance at 450 nm was measured using a microplate reader. The controls used were cells without any treatment, cells treated with ALA without illumination (in the dark) and cells treated with light alone. The percentage was calculated based on the value of untreated controls.

Virus isolation in vivo. Specimens for viral cultures were taken from lesions on the backs of guinea pigs by gently rubbing a cotton-tipped swab over the lesions and placing them into 2 ml of transport medium. The specimens were transferred immediately to the laboratory. For viral culture the swabs were agitated and inoculated into tubes containing monolayers of human embryo fibroblasts (Vero) or green monkey kidney cells, pretreated with 10 µM dexamethazone. After incubation at 37° C. for 24 hours the medium was replaced with fresh Eagle's minimal essential medium supplemented with nonessential amino acids (MEII-NAA) containing 2% fetal calf serum. The cultures were examined for cytopathic effect (CPE). When the cells showed 50% CPE they were harvested, washed and used to prepare slides for immunofluorescent staining for HSV confirmation.

Light exposure. The light source used in the experiments was a 500 W xenon short arc lamp (Versa Light, Medic Lightech, Ltd. Haifa, Israel) filtered to isolate a wideband red light (590–700 nm) and transmitted via a fiber bundle at an irradiance of 100 mW/cm$^2$.

Animals. Both male and female Hartley guinea pigs weighing 200–300 g were used in the animal experiments. In each experiment, 5–10 animals were used.

Chemicals and application. ALA was obtained from Sigma Chemical Co. (St. Louis, Mo.). For in vitro cell line experiments, ALA was dissolved in PBS and added to the cells at 1 mM final concentration, unless indicated otherwise. For animal experiments, ALA was administered intraperitoneally at 240 mg/kg body weight, at various times after infection with HSV. Animals were exposed to light 3 hours after ALA administration. For human clinical experiments, 20% of ALA, 2% DMSO and 2% EDTA disodium salt in base cream was applied to the lesion (0.2 ml ALA cream per 1 cm$^2$ of skin area) after cleaning the area with saline solution. After the ALA cream application, the skin was covered by a plastic adhesive dressing and an aluminum foil shield for protection from light exposure. The cream was left on the skin 4–5 hours. Prior to light exposure the ALA cream was removed.

Protoporphyrin (PP) fluorescence measurements. To observe the production of PP in the lesion after ALA application, the red fluorescence of PP was photographed during illumination of the area with a medical-surgery UV examining light source (Burton Division, Cavitron Corp., Van Nuys, Calif.).

Results

In Vitro Experiments

Figure 2:
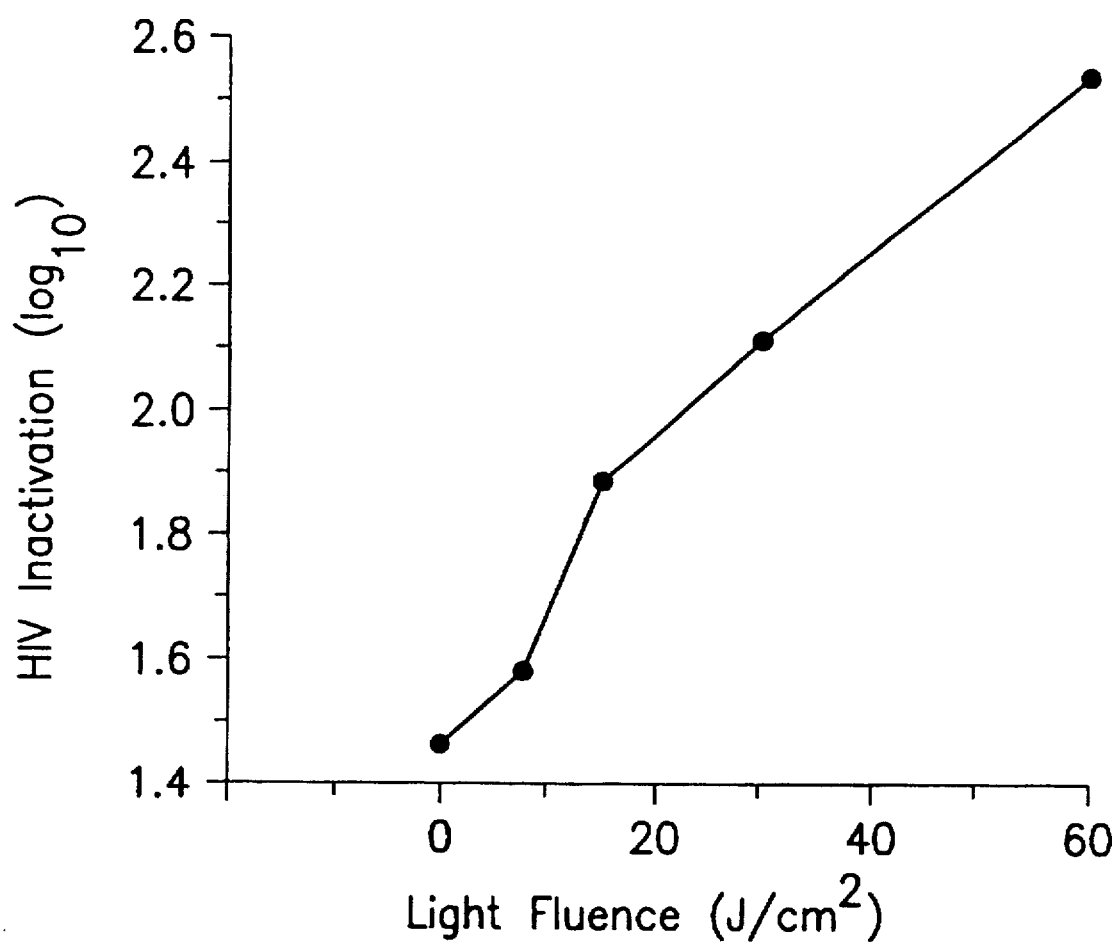
FIG. 2 represents HIV inactivation in U1 cells grown with 1 mM ALA and 50 μM desferal for 5 hours followed by exposure to graded doses of red light at a fluence rate of 25 mW/cm$^2$. HIV titer was assayed as described in Materials and Methods.

In order for ALA-PDT to be effective, ALA concentration and time of incubation was optimized to obtain maximal accumulation of PP in the cells. In most cases it takes 3–6 hr to reach the peak of PP accumulation and in our preliminary studies we found that in U1 cells latently infected with HIV, this peak occurs when ALA was added at 1 mM to the growth medium. This accumulation is further enhanced approximately 2-fold when desferal was also added (FIG. 1). This is consistent with previous observations (Linuma, S., et al., *Br. J. Cancer* 70:21–28 (1994)) and is due to chelation of iron by desferal, which inhibits conversion of PP to haem by ferrochelatase. For subsequent experiments 1 mM ALA, 50 µM desferal and 5 hour incubation was used to maximize the effect. FIG. 2 shows that under these conditions about 1.5 log$_{10}$ inactivation of HIV occurs in U1 cells. Exposure to light progressively inactivated HIV as a function of light dose, reducing HIV titer by 2.6 log$_{10}$ at 60 J/cm$^2$.

Figure 3:
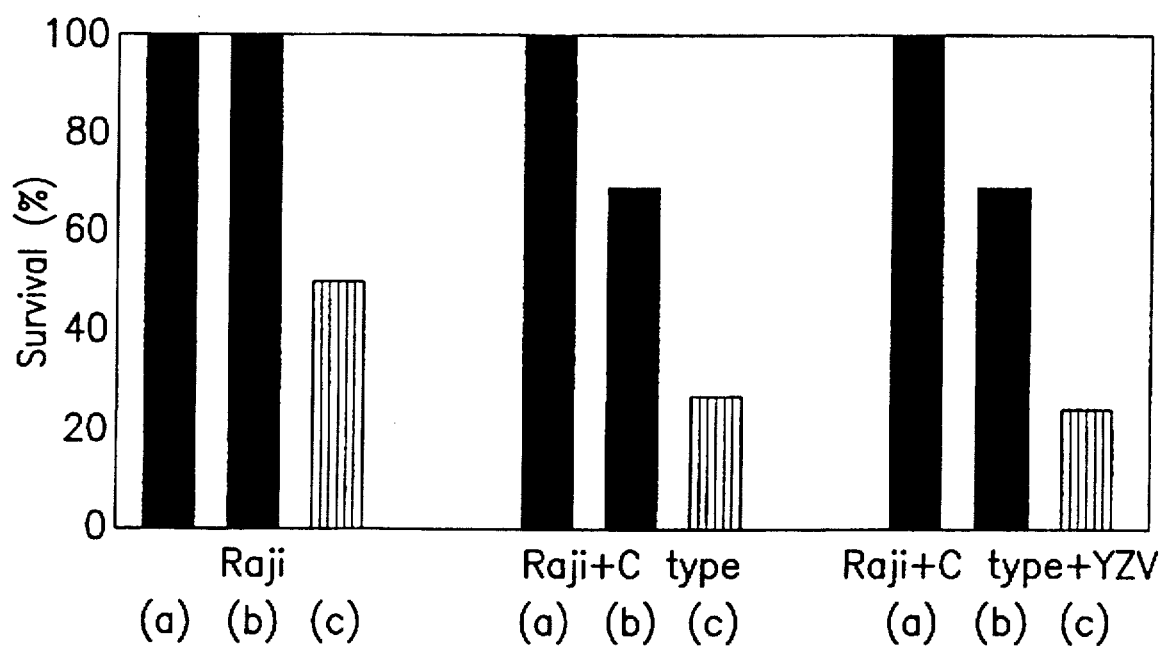
FIG. 3 represents the percentage of cell survival of (1) Raji alone, (2) Raji+C type retrovirus, and (3) Raji+C type retrovirus+Varicella zoster virus (VZV), incubated without ALA (control, a), incubated with ALA for 5 hours and kept in the dark (b), and incubated with 1 mM ALA for 5 hours and exposed to red light at 18 J/cm$^2$ (c). Cell survival was determined as described in Materials and Methods.
Figure 4:
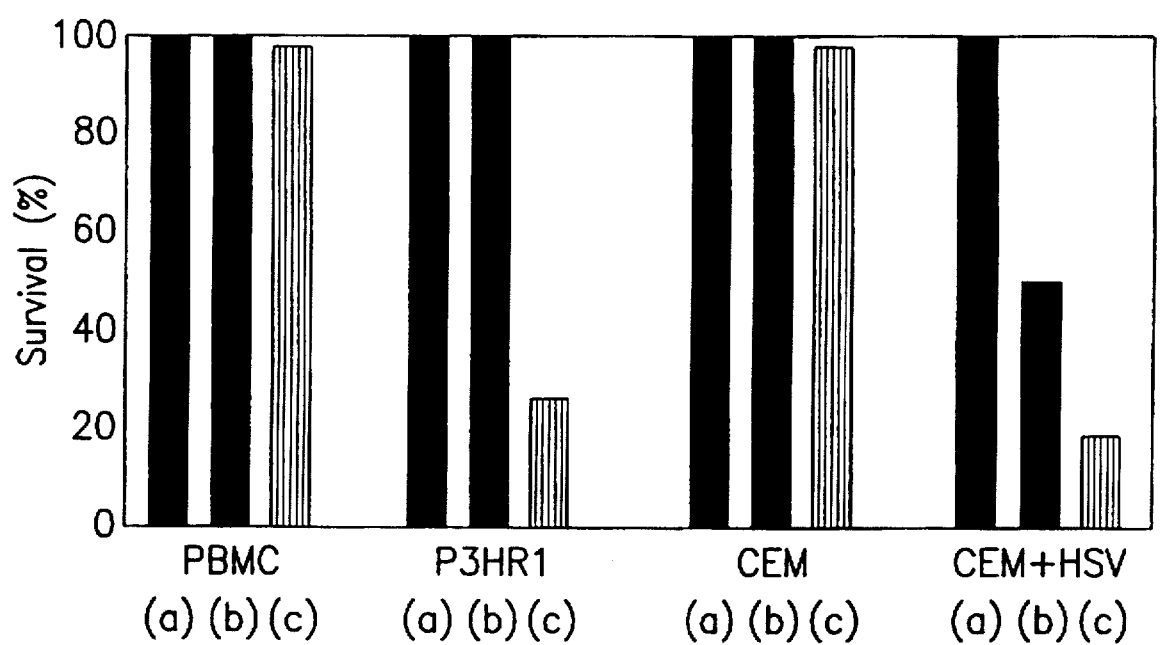
FIG. 4 represents the percentage of cell survival of (1) peripheral blood mononuclear cells (PBMC), (2) P3HR1+ Ebstein-Barr virus (EBV), (3) CEM alone, and (4) CEM+ herpes simplex virus type-1 (HSV), incubated without ALA (control, a), incubated with 1 mM ALA for 5 hours and kept in the dark (b), and incubated with 1 mM ALA for 5 hours and exposed to red light at 18 J/cm$^2$ (c). Cell survival was determined as described in Materials and Methods.

The generality of this phenomenon was established for other viruses harbored in lymphoblastoid cells. FIG. 3 shows that ALA-PDT reduced survival of Raji cells infected with a C-type retrovirus and VZV to about 25% of control cells not treated with ALA. Again, some reduction was also observed with ALA in the dark. The uninfected cells were not affected in the dark and only moderately affected by ALA-PDT. The effects of ALA-PDT on P3HR1 cells infected with EBV and on CEM cells infected with HSV are shown in FIG. 4. Dramatic destruction of the infected cells was observed while little or no effect was seen on uninfected cells (FIG. 4).

Animal Studies

Clinical observations. Inoculation of HSV on the backs of guinea. pigs resulted in a local infection starting after 24 hours. manifested as reddening and swelling for up to 3 days. At 3–6 days vesicles were formed followed by the appearance of crusts during the 2nd week. Complete healing occurred at 3–4 weeks after infection. Exposure to light or ALA only at various times after infection had no significant effect on the clinical manifestations. When treated with ALA-PDT immediately or up to 6 hours after infection there was a dramatic effect. Duration of vesicles' appearance was very short and healing started on the 3rd day. Crusting time, however, was longerhand the diameter of the crusts was 2 cm instead of 0.3–0.5 cm in the controls. The crusts remained for about a month and the irradiated area remained hairless for 6 weeks. ALA-PDT administered 24 hours or longer after infection had no effect on the manifested signs.

Figure 5:
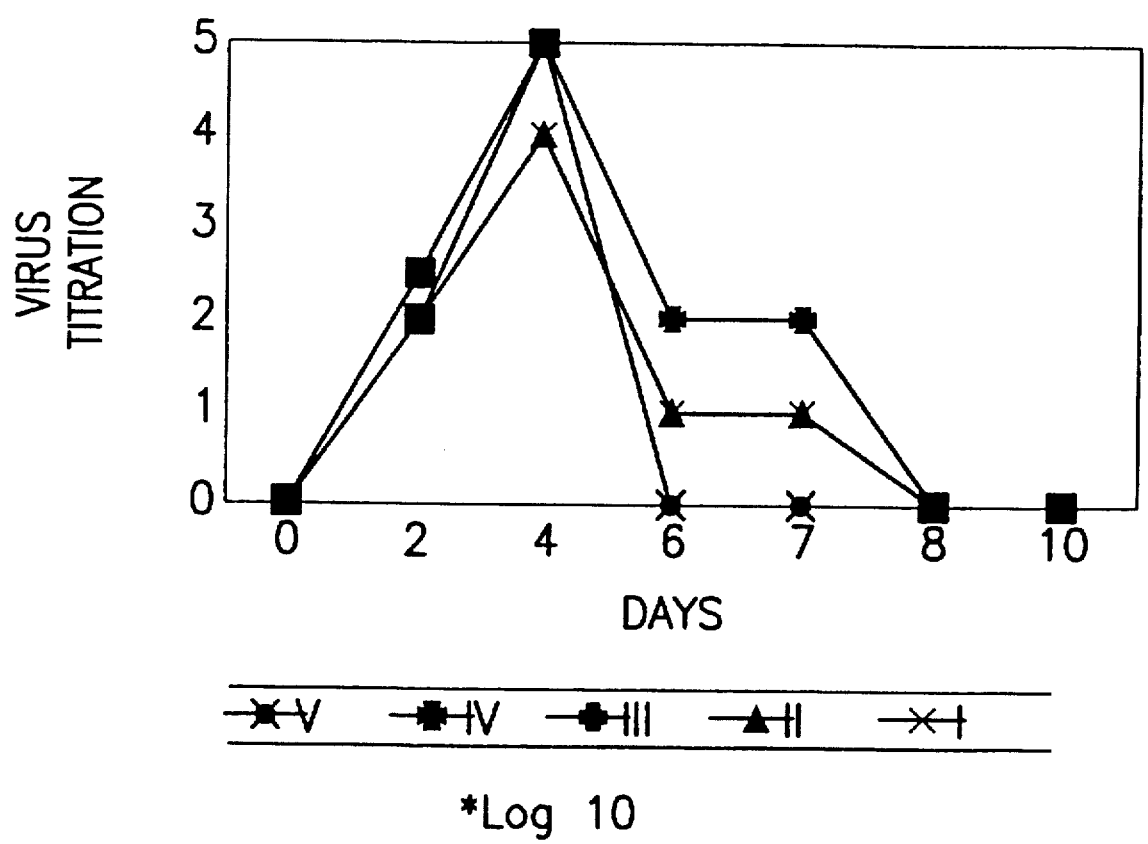
FIG. 5 represents HSV titration in control group of Guinea pigs I-V infected with HSV, at different days after infection. HSV (Log$_{10}$) was titrated as described in Materials and Methods.
Figure 6:
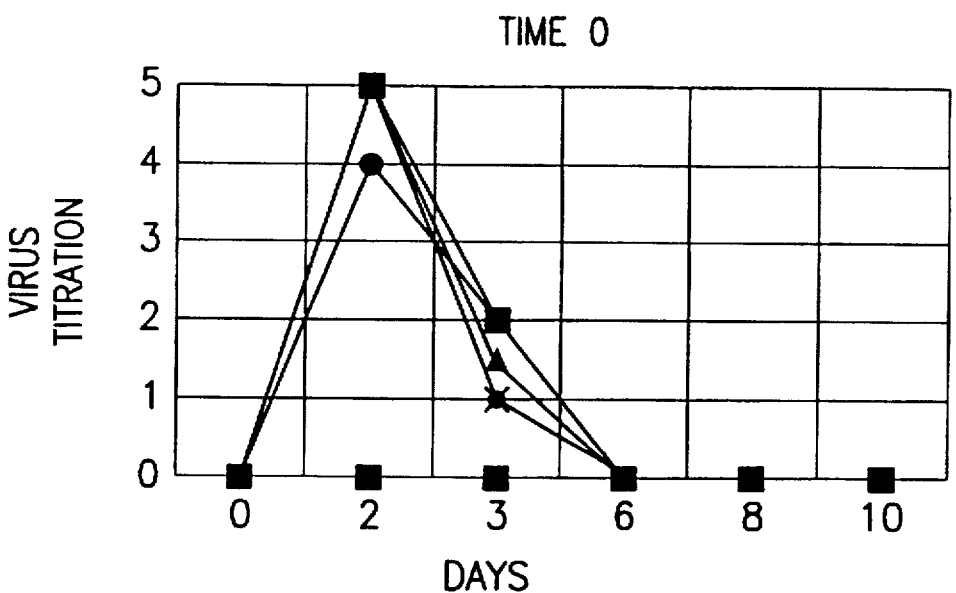
FIG. 6 represents HSV titration of Guinea pigs I-X infected with HSV and shortly thereafter administered 240 mg/kg ALA intraperitoneally. The infected area of Guinea pigs I-V was then exposed 3 hours later with 120 J/cm$^2$ of red light. Animals VI-X served as dark control. HSV (Log$_{10}$) was titrated as described in Materials and Methods.
Figure 7:
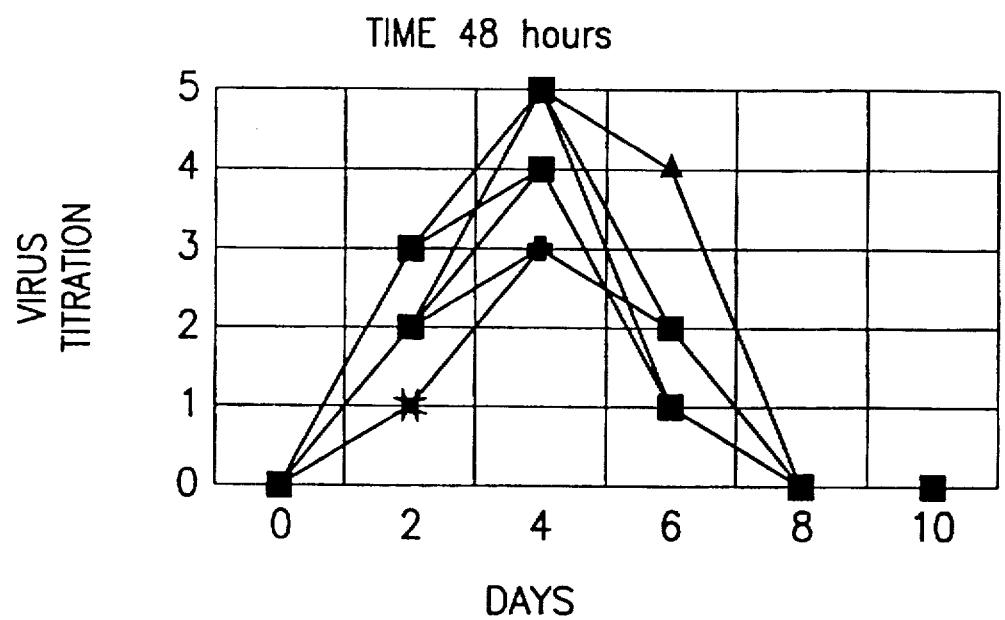
FIG. 7 represents HSV titration of Guinea pigs I-X infected with HSV and administered 240 mg/kg ALA intraperitoneally two days after infection. The infected area of Guinea pigs I-V was then exposed 3 hours later with 120 J/cm$^2$ of red light. Animals VI-X served as dark control. HSV (Log$_{10}$) was titrated as described in Materials and Methods.

Virus titration. The clinical observations were confirmed by titrating HSV isolated after infection. FIG. 5 shows that HSV titer reached a peak of 5 $\log_{10}$ TCID$_{50}$ (tissue culture infectious dose at 50% of the cultures) 4 days after infection. on the sixth day no virus could be isolated. Similar kinetics were observed when ALA was administered immediately after infection (FIG. 6). However, when ALA administration was followed by 120 J/cm$^2$ light exposure no HSV could be isolated. ALA-PDT 2 days after infection had only a small effect on the HSV titer (FIG. 7).

Human Clinical cases

Case 1. A patient who underwent kidney transplant 15 years ago exhibited massive Verrucae vulgares of the hands. ALA (20%) in cream supplemented with EDTA and DMSO was applied, and the area was exposed to red light 4 hours later (120 J/cm$^2$). Within 7 days from treatment, crusts were formed. A dramatic clearance of the lesions was seen 1 month after treatment.

Case 2. An AIDS patient presented with *Molluscum contagiosum* was treated with ALA/red light as described above in Case 1. Dramatic regression of the lesions was seen one month after 120 J/cm$^2$ of red light.

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A method for treating a viral skin infection in a subject comprising topically applying to the skin infection of the subject in need there of a topical pharmaceutical composition comprising 5-aminolevulinic acid and an iron chelating agent in amounts effective to cause virus-infected skin cells to accumulate protoporphyrin such that upon application of a sufficient dose of red light, the virus-infected, protoporphyrin-accumulated skin cells will be destroyed; and applying a sufficient dose of red light to the virus-infected, protoporphyrin-accumulated skin cells to destroy the virus-infected, protoporphyrin-accumulated skin cells.

2. The method of claim 1, wherein the virus-infected skin cells are infected with a virus selected from the group consisting of herpes simplex virus, *Molluscum contagiosum*, human immunodeficiency virus, *Varicella zoster* virus, C-type retrovirus, Ebstein-Barr virus, cytomegalovirus and papillomavirus.

3. The method of claim 1, wherein the iron chelating agent is selected from the group consisting of EDTA and desferal.

4. The method of claim 1, wherein the amount of protoporphyrin accumulated is between about 20 pmoles and about 100 pmoles per $10^6$ cells.

5. The method of claim 1, wherein the red light applied has a wavelength of about 630 nm.

6. The method of claim 1, wherein the red light applied has a wavelength of about 590–700 nm.

* * * * *

UNITED STATES PATENT AND TRADEMARK OFFICE
CERTIFICATE OF CORRECTION

PATENT NO. : 5,895,786
DATED : April 20, 1999
INVENTOR(S) : Ehud Ben-Hur

It is certified that error appears in the above-identified patent and that said Letters Patent is hereby corrected as shown below:

Title page, item [73] Assignee: add Bar-Ilan University.

Signed and Sealed this

Nineteenth Day of October, 1999

Attest:

Q. TODD DICKINSON

Attesting Officer

Acting Commissioner of Patents and Trademarks